(12) United States Patent
Di Florio

(10) Patent No.: US 12,721,943 B2
(45) Date of Patent: Sep. 1, 2026

(54) DEVICE ASSEMBLY FOR THE INFUSION OF MEDICAL SOLUTIONS

(71) Applicant: ADRIA.MED. S.R.L., Tocco da Casauria (IT)

(72) Inventor: Francesco Di Florio, Tocco da Casauria (IT)

(73) Assignee: ADRIA.MED. S.R.L., Tocca da Casauria (IT)

( * ) Notice: Subject to any disclaimer, the term of this patent is extended or adjusted under 35 U.S.C. 154(b) by 532 days.

(21) Appl. No.: 18/258,161

(22) PCT Filed: Dec. 17, 2021

(86) PCT No.: PCT/IB2021/061903
§ 371 (c)(1),
(2) Date: Jun. 16, 2023

(87) PCT Pub. No.: WO2022/137050
PCT Pub. Date: Jun. 30, 2022

(65) Prior Publication Data

US 2024/0075201 A1 Mar. 7, 2024

(30) Foreign Application Priority Data

Dec. 21, 2020 (IT) ........................ 102020000031637

(51) Int. Cl.
*A61M 5/14* (2006.01)
*A61M 5/145* (2006.01)
(Continued)

(52) U.S. Cl.
CPC .......... *A61M 5/1413* (2013.01); *A61M 5/152* (2013.01); *A61M 5/1414* (2013.01); *A61M 5/14586* (2013.01); *F04B 43/084* (2013.01)

(58) Field of Classification Search
CPC .. A61M 5/1413; A61M 5/152; A61M 5/1414; A61M 5/14586; F04B 43/084
See application file for complete search history.

(56) References Cited

U.S. PATENT DOCUMENTS 5,211,632 A * 5/1993 Tsukada ................ A61M 5/152 604/246
5,284,481 A 2/1994 Soika
(Continued)

FOREIGN PATENT DOCUMENTS

EP 0426319 A2 5/1991
EP 3248633 A1 * 11/2017 ............ A61M 5/152

OTHER PUBLICATIONS

International Search Report and Written Opinion received for PCT Application No. PCT/IB2021/061903, on Mar. 17, 2022, 10 pgs.
(Continued)

*Primary Examiner* — David N Brandt
(74) *Attorney, Agent, or Firm* — Merchant & Gould P.C.

(57) ABSTRACT

A device is for the infusion of medical solutions containing drugs or other physiologically useful substances. The medical solution infusion device assembly includes an infusion device and a housing containing it. The infusion device includes an elastomeric pump having a closed end and an open end, a cannula and a filling valve configured to fill the elastomeric pump with a medical solution. The housing of the infusion device has a first half-shell and a second half-shell, configured to be sealingly coupled to each other and to the infusion device. The sealed coupling with the infusion device is arranged in a position adjacent to the open end of the elastomeric pump.

13 Claims, 7 Drawing Sheets

(51) Int. Cl.
*A61M 5/152* (2006.01)
*F04B 43/08* (2006.01)

(56) References Cited

U.S. PATENT DOCUMENTS

| | | | | |
|---|---|---|---|---|
| 2006/0150725 | A1* | 7/2006 | Yamada | A61M 5/16845 604/246 |
| 2006/0229558 | A1* | 10/2006 | Heston | A61M 5/152 604/131 |
| 2007/0156103 | A1* | 7/2007 | Chatlynne | A61M 5/152 604/257 |
| 2007/0232747 | A1* | 10/2007 | Maris | C08L 53/025 524/505 |
| 2014/0228758 | A1* | 8/2014 | Chi | A61M 5/152 604/132 |
| 2019/0105464 | A1* | 4/2019 | Naidu | A61M 25/0606 |

OTHER PUBLICATIONS

Italian Application as Filed; Italian Publication No. 1425596, published Feb. 1, 2016, 19 pgs.
Italian Application as Filed; Italian Serial No. 102016000054191, filed May 26, 2016, 25 pgs.

* cited by examiner 3a
24
15
21
25
21a
24
17
19
23
26
18
22
20

3a
29
16
30
13
27
29
28
14
23

36
32
31
15a
33
17a
18a
20a
31a
22a
19a
23a 36
30a
16a
16b
13a
14a
23a 1
30
29
3a
36
27
29
13
10
14
6
3b
17a
4
4b
5
25
17
3a
33
25a
25a
31
3b
21
32
24
3a

DEVICE ASSEMBLY FOR THE INFUSION OF MEDICAL SOLUTIONS

CROSS-REFERENCE TO RELATED APPLICATIONS

This application is a national stage of International Application No. PCT/IB2021/061903, filed on Dec. 17, 2021, which claims priority to Serial No. 10 2020 000031637, filed Dec. 21, 2020 with the Italian Patent Office, which are incorporated herein by reference of their entirety.

FIELD OF THE INVENTION

The present invention relates to a device for the infusion of medical solutions containing drugs or other physiologically useful substances.

PRIOR ART

Portable devices for the infusion of medical solutions are widely used. They normally comprise an elastomeric pump, i.e., a device which allows the continuous delivery of a medical solution at a substantially constant and predetermined flow rate.

There has been a real revolution in the field with the advent of elastomeric pumps. In fact, this technology has made it possible to achieve exceptional results in terms of precision and constant infusion at significantly reduced costs with respect to the previously used electronic pumps. Furthermore, the possibility of using the device even outside healthcare facilities has allowed a significant reduction in hospitalization costs.

The elastomeric pump consists of a tank which has the shape of a balloon made of elastomeric material designed to ideally exert an almost constant pressure on the fluid contained therein. Such fluid is pushed along an infusion line directly into the vein, under the skin, around a plexus, into a joint or in epidural, as needed.

In some models, a cylinder-piston system connected to the infusion line is placed inside the elastomeric pump, in order to facilitate the return to the original position.

The solution contained in the tank reaches the patient through said infusion line, the distal end of which (i.e., the patient side) has a flow restrictor which, based on the section/length thereof, determines the hourly flow of the system.

The elastomeric pumps are mechanically activated and operated, they do not require programming as the flow is preset, they do not need batteries nor to be connected to an electricity source, they are reliable and have high safety standards. However, assembling them is cumbersome, requiring various steps of gluing or welding the various parts, especially in the case of elastomeric pumps provided with a cylinder-piston system.

SUMMARY OF THE INVENTION

Therefore, it is an object of the invention to provide a device for the infusion of a medical solution which is easy to assemble, in the sense that the operations required for the construction thereof are minimized, and which is simultaneously reliable and low-cost.

Such an object is achieved by an infusion device assembly as outlined in the appended claims, the definitions of which form an integral part of the present description.

Therefore, the invention relates to a medical solution infusion device assembly, comprising an infusion device and a housing containing it, in which the infusion device comprises an elastomeric pump having a closed end and an open end, a cannula and a filling valve, configured for filling the elastomeric pump with a medical solution, characterized in that the infusion device housing comprises a first half-shell and a second half-shell, configured to be sealingly coupled to each other and to the infusion device, the sealed coupling with the infusion device being arranged in a position adjacent to the open end of the elastomeric pump.

BRIEF DESCRIPTION OF THE DRAWINGS

Further features and advantages of the present invention will become more apparent from the description of certain embodiments thereof, given hereafter only by way of a non-limiting, indicative example, with reference to the following figures.

DETAILED DESCRIPTION OF THE INVENTION

Figure 1:
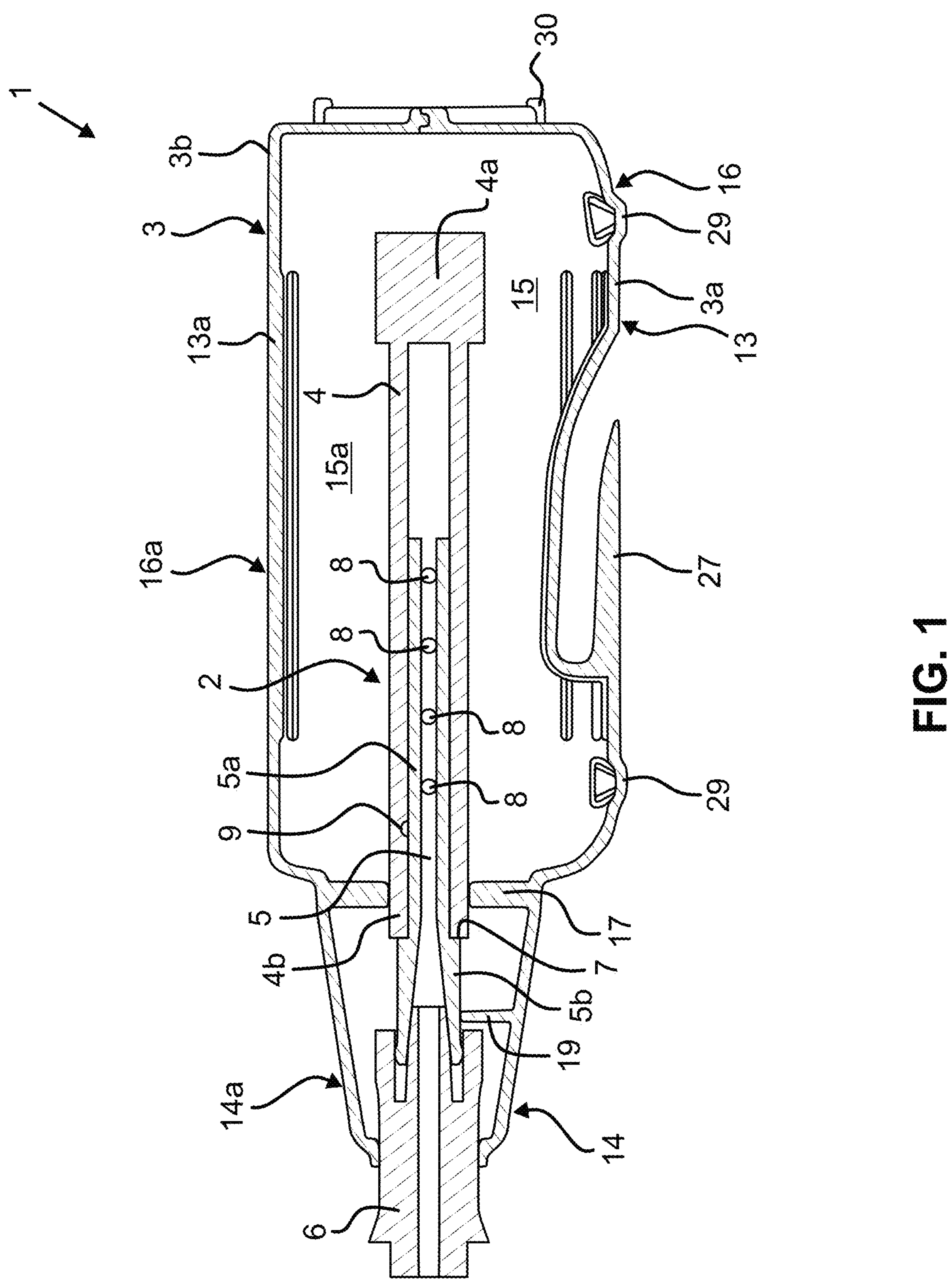
FIG. 1 depicts a longitudinal sectional view of the infusion device assembly according to the invention.

With reference to the figures, the infusion device assembly according to the invention, indicated as a whole with the number 1, comprises an infusion device 2 and a housing 3 containing it.

The infusion device 2 comprises an elastomeric pump 4, a cannula 5 and a filling valve 6, configured for filling the elastomeric pump 4 with a medical solution.

The elastomeric pump 4 is of a known type and can be selected from the elastomeric pumps generally used for the infusion of medical solutions. For example, elastomeric pumps of this type are known from patents IT 1 425 596 and IT 102016000054191 of the same Applicant.

The elastomeric pump 4 is tubular in shape and comprises a closed end 4*a* and an open end 4*b*.

The elastomeric pump 4 is made of a thermoplastic elastomer and is PVC (polyvinyl chloride) free. The preferred elastomeric material is a hydrogenated polystyrene block copolymer with polyolefins (HSBS). Preferably, such polymers have a Shore A hardness of about 35 and a Shore D hardness of about 55.

Figure 5:
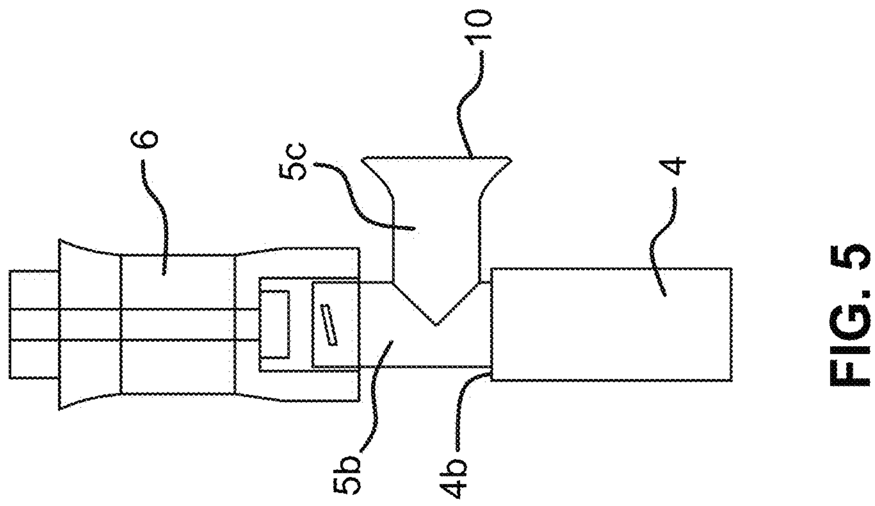
FIG. 5 depicts a side view of a detail of the infusion device according to the invention in a pre-assembled condition.
Figure 4:
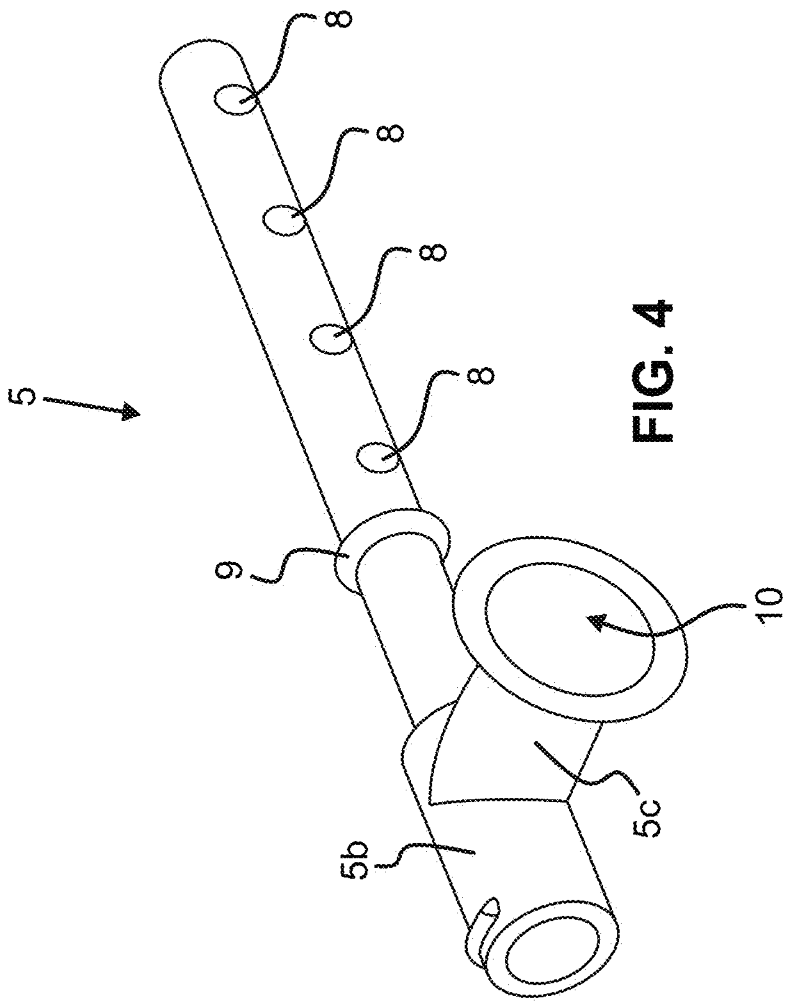
FIG. 4 depicts a perspective view of a detail of the infusion device according to the invention.

The cannula 5, also shown in FIG. 4 and partially in FIG. 5, comprises a first tubular portion 5*a*, a second tubular portion 5*b* and a fitting 5*c* protruding perpendicularly at the second tubular portion 5*b*.

The first tubular portion 5*a* has a smaller diameter than the diameter of the second tubular portion 5*b*, so that a shoulder 7 is placed at the junction of the two portions 5*a*, 5*b*. The first tubular portion 5*a* is configured to fit inside the elastomeric pump 4, the open end 4*b* of which abuts against the shoulder 7.

The first tubular portion 5*a* comprises a plurality of through holes 8 which put the interior of the cannula 5 in communication with the interior of the elastomeric pump 4, allowing the filling and emptying thereof.

The first tubular portion 5*a* further comprises a protruding ring 9 which has the function of improving the retention and seal of the elastomeric pump 4 on the cannula 5.

The second tubular portion 5*b* is configured to couple by screwing with the valve 6, as shown in FIGS. 1 and 5. The valve 6 of a conventional type is a needleless unidirectional access valve which only allows filling the elastomeric pump 4 by means of the cannula 5, but does not allow the return of liquid.

The fitting 5*c* originates from the second tubular portion 5*b* of the cannula 5 and extends perpendicular thereto, ending with an open end 10, preferably flared in shape, configured to couple with an infusion line, for example a catheter carrying the medical solution to a patient.

Figure 9:
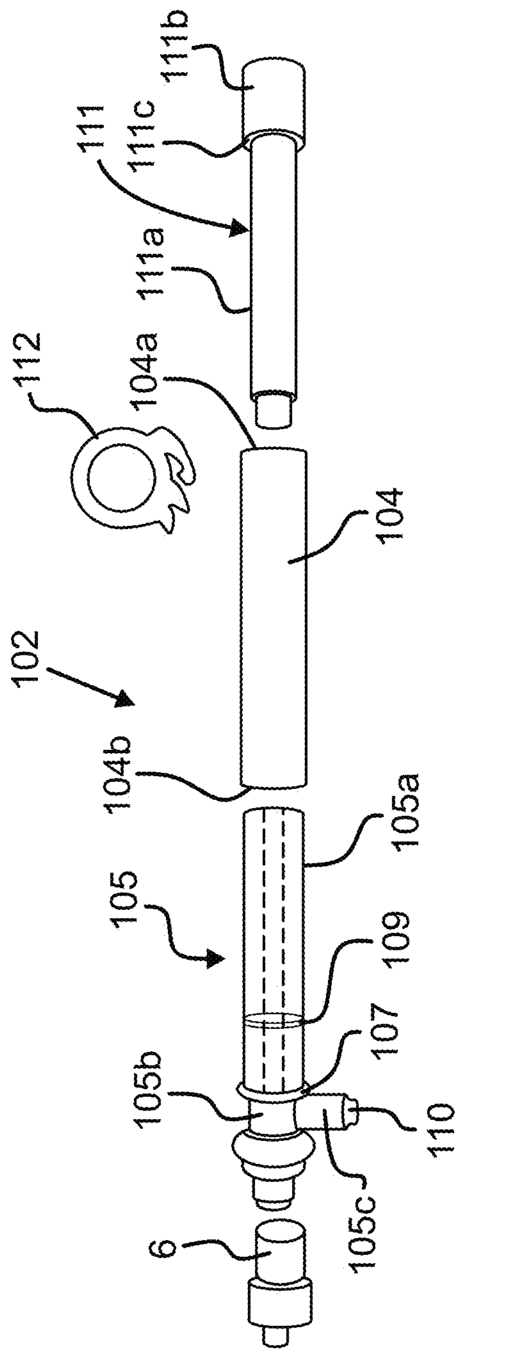
FIG. 9 depicts an exploded side view of a variant of the infusion device according to the invention.
Figure 10:
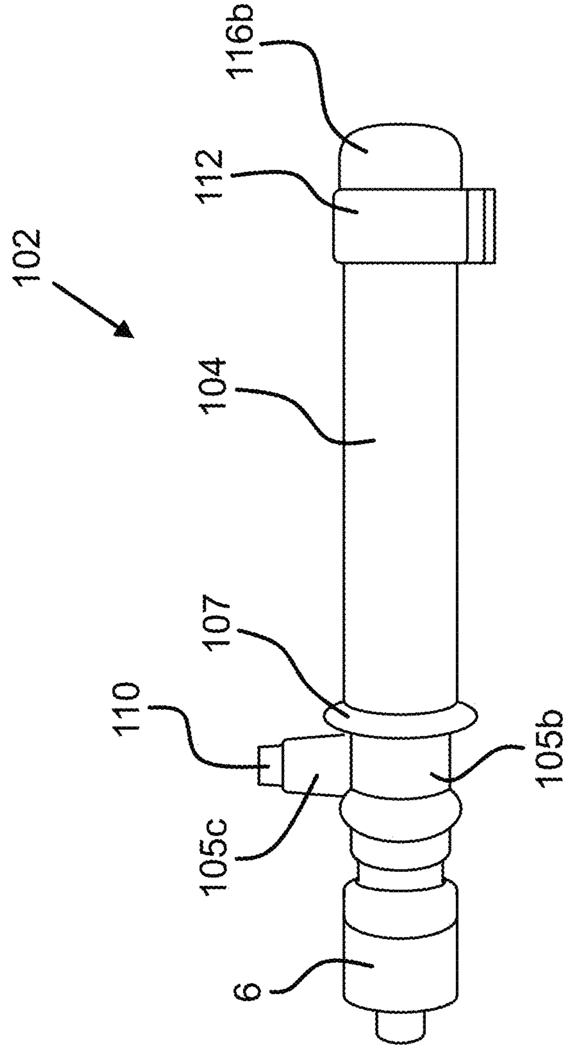
FIG. 10 depicts a side view of the infusion device in FIG. 9 in an assembled condition.

A different embodiment of the infusion device, indicated with the number 102, is shown in FIGS. 9 and 10.

The infusion device 102 comprises an elastomeric pump 104, a cannula 105 substantially similar to the cannula 5 described above, a filling valve 6 as described above, and a piston 111.

Therefore, the cannula 105 comprises a first tubular portion 105*a*, a second tubular portion 105*b* of greater diameter, a fitting 105*c* placed perpendicularly to the second tubular portion 105*b*, a protruding sealing ring 109 and a shoulder 107 placed at the junction between the first and second tubular portions 105*a*, 105*b*.

The cannula 5, 105, in both the first and in the second version, is preferably made in one piece.

The piston 111 comprises a first portion 111*a*, configured so as to be fitted in both the elastomeric pump 104 and in the first portion 105*a* of the cannula 105, and a second portion 111*b* of larger diameter, a shoulder 111*c* being placed between the two portions 111*a*, 111*b*.

The elastomeric pump 104 initially has both ends 104*a*, 104*b* open, but one end 104*a* is closed by the second portion 111*b* of the piston 111, abutting against the respective shoulder 111*c*. A welding band 112 allows the end 104*a* of the elastomeric pump 104 to be tightly clamped onto the piston 111, as shown in FIG. 10 (assembled infusion device). Therefore, also in this embodiment, the elastomeric pump 104 will have a closed end 104*a*.

This type of infusion device is known per se. When the elastomeric pump 104 is filled with the medical solution, it tends to swell and stretch. Therefore, the piston 111 is extracted from the interior of the cannula 105 and positions itself in an extended condition. During infusion, the elastomeric pump 104 returns to shorten and the piston 111 returns to the cannula 105.

The housing 3 of the infusion device 2 comprises a first half-shell 3*a* and a second half-shell 3*b*. The half-shells 3*a*, 3*b* are configured to sealingly couple to each other and to the infusion device 2, 102. The sealed coupling with the infusion device 2, 102 is arranged in a position adjacent to the open end 4*b*, 104*b* of the elastomeric pump 4, 104.

Figures 2A, 2B:
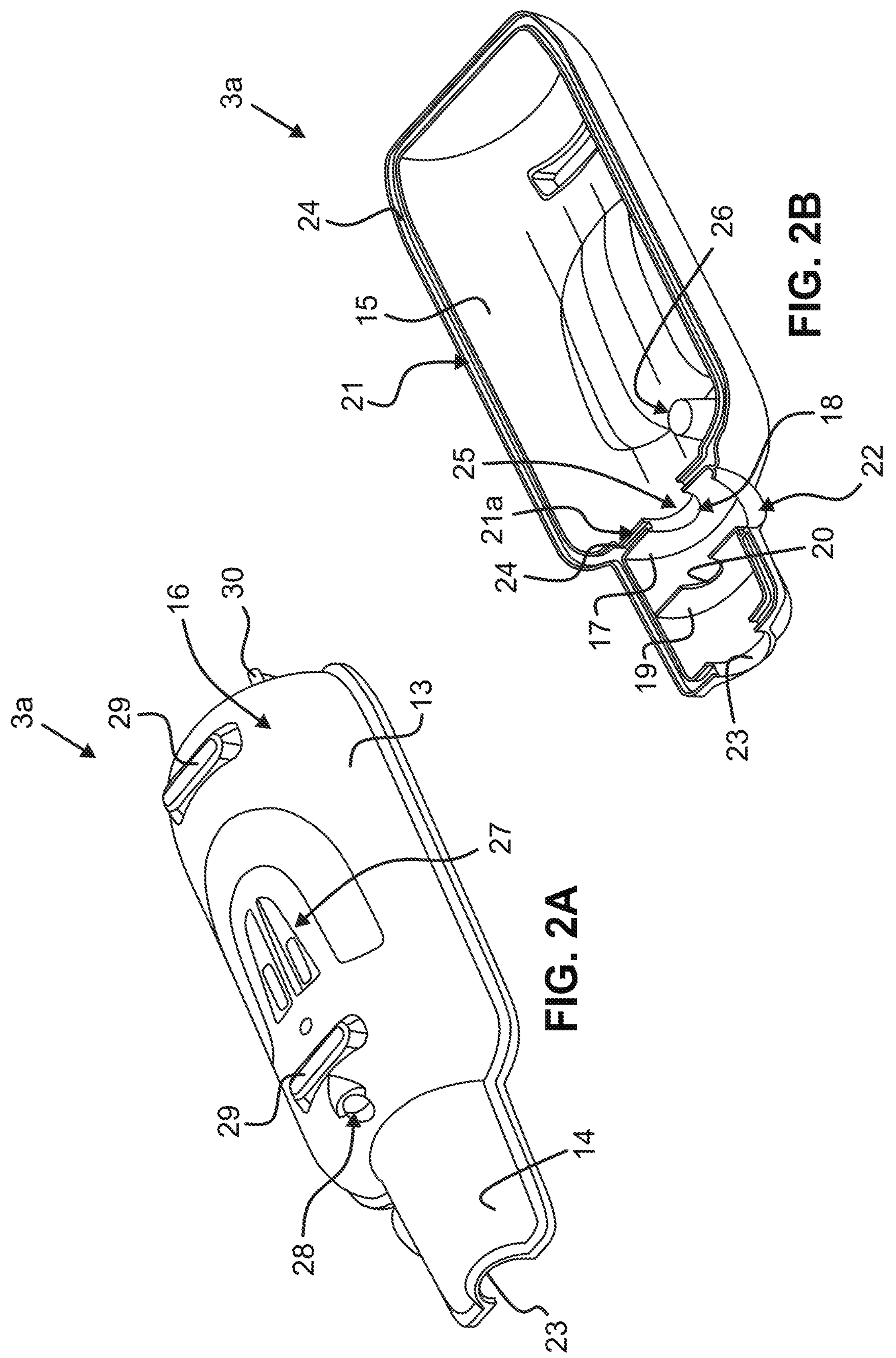
FIG. 2A depicts a perspective view of a first half-shell of the assembly in FIG. 1.
FIG. 2B depicts a perspective view of the half-shell in FIG. 2A from a different point of view.

The first half-shell 3*a*, shown in FIGS. 2A and 2B, is formed by a first shell portion 13 of greater width and a second shell portion 14 of smaller width and comprises an inner surface 15, an outer surface 16 and an edge 21 connecting them. The first shell portion 13 is configured to accommodate the elastomeric pump 4, 104, while the second shell portion 14 is configured to accommodate the assembly formed by the open end 4*b*, 104*b* of the elastomeric pump 4, 104, by the second tubular portion 5*b*, 105*b* of the cannula 5, 105 with the fitting 5*c*, 105*c* and by the filling valve 6.

Figures 6, 7, 8:
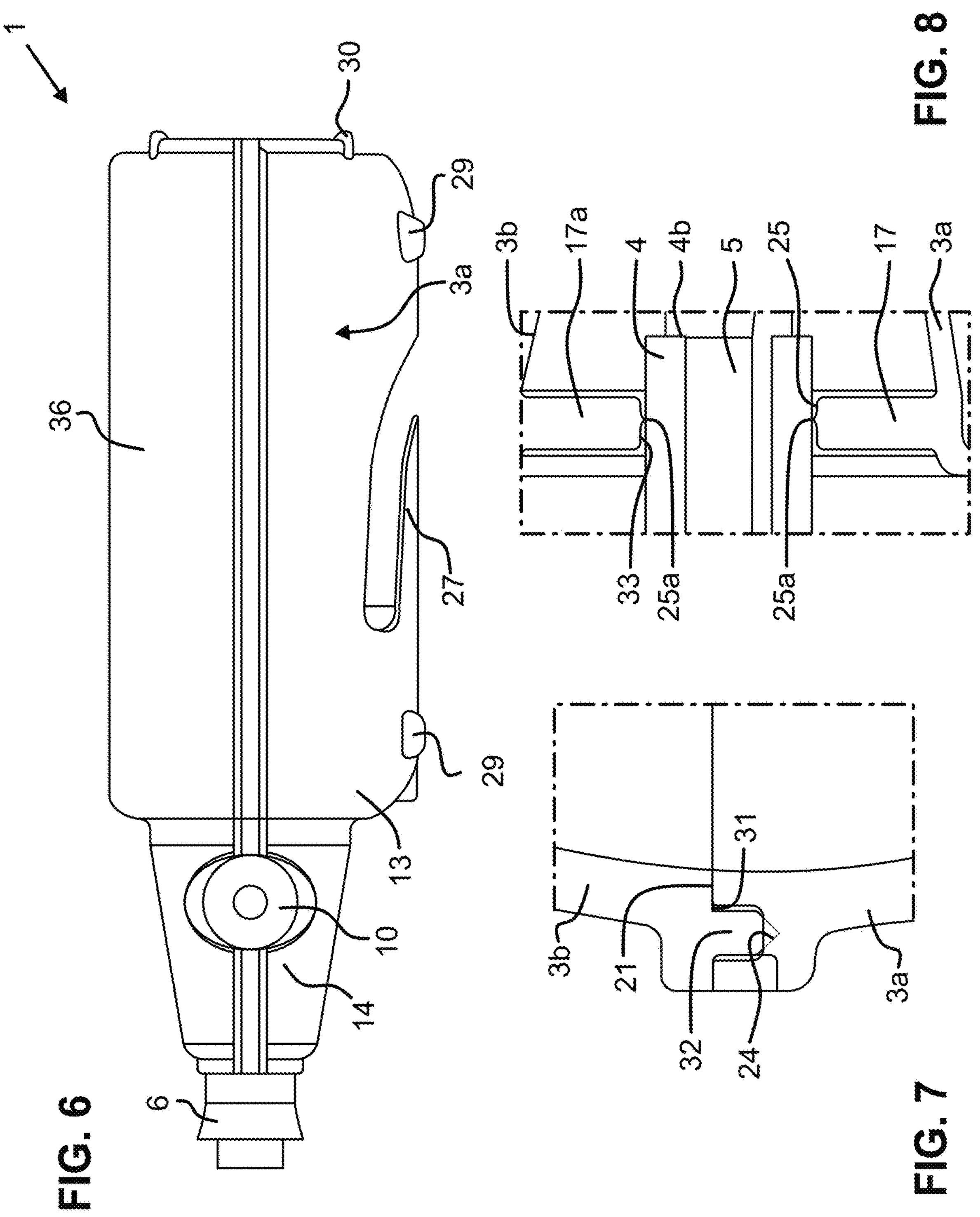
FIG. 6 depicts a side view of the assembly according to the invention in an assembled condition.
FIG. 7 depicts a sectional view of a detail of the assembly in FIG. 6.
FIG. 8 depicts a sectional view of a different detail of the assembly in FIG. 6.

The edge 21 comprises a groove 24, visible in FIG. 7, which runs along the perimeter of the half-shell 3*a*.

The inner surface 15, at the junction point between the first shell portion 13 and the second shell portion 14, comprises a first rib 17 comprising a semicircular recess 18, of such shape and size as to accommodate a semi-cylindrical portion of the assembly formed by the elastomeric pump 4, 104 and the second tubular portion 5*b*, 105*b* of the cannula 5, 105. The edge 21*a* of the first rib 17 comprises a groove 24 in continuation of the groove 24 placed on the edge 21 of the half-shell 3*a*. Conversely, the edge 25 of the recess 18 comprises a ridge 25*a* (FIG. 8).

The inner surface 15 of the second shell-like portion 14 further comprises a second rib 19 comprising a respective recess 20 of such shape and size as to accommodate a semi-cylindrical portion of the assembly formed by the second tubular portion 5*b*, 105*b* of the cannula 5, 105 and the valve filling 6.

At the second shell-like portion 14, the edge 21 comprises a first semicircular groove 22 to house the open end of the fitting 5*c*, 105*c* of the cannula 5, 105 and a second semicircular groove 23 to house the filling valve 6.

The inner surface 15 of the first half-shell 3*a* further comprises a seat 26 for a hygroscopic filter.

In embodiments, the outer surface 16 of the first half-shell 3*a* comprises a hook 27 for the suspension of the assembly 1, a seat 28 for a strap and feet 29, 30, respectively for the horizontal or vertical support of the assembly 1.

Figures 3A, 3B:
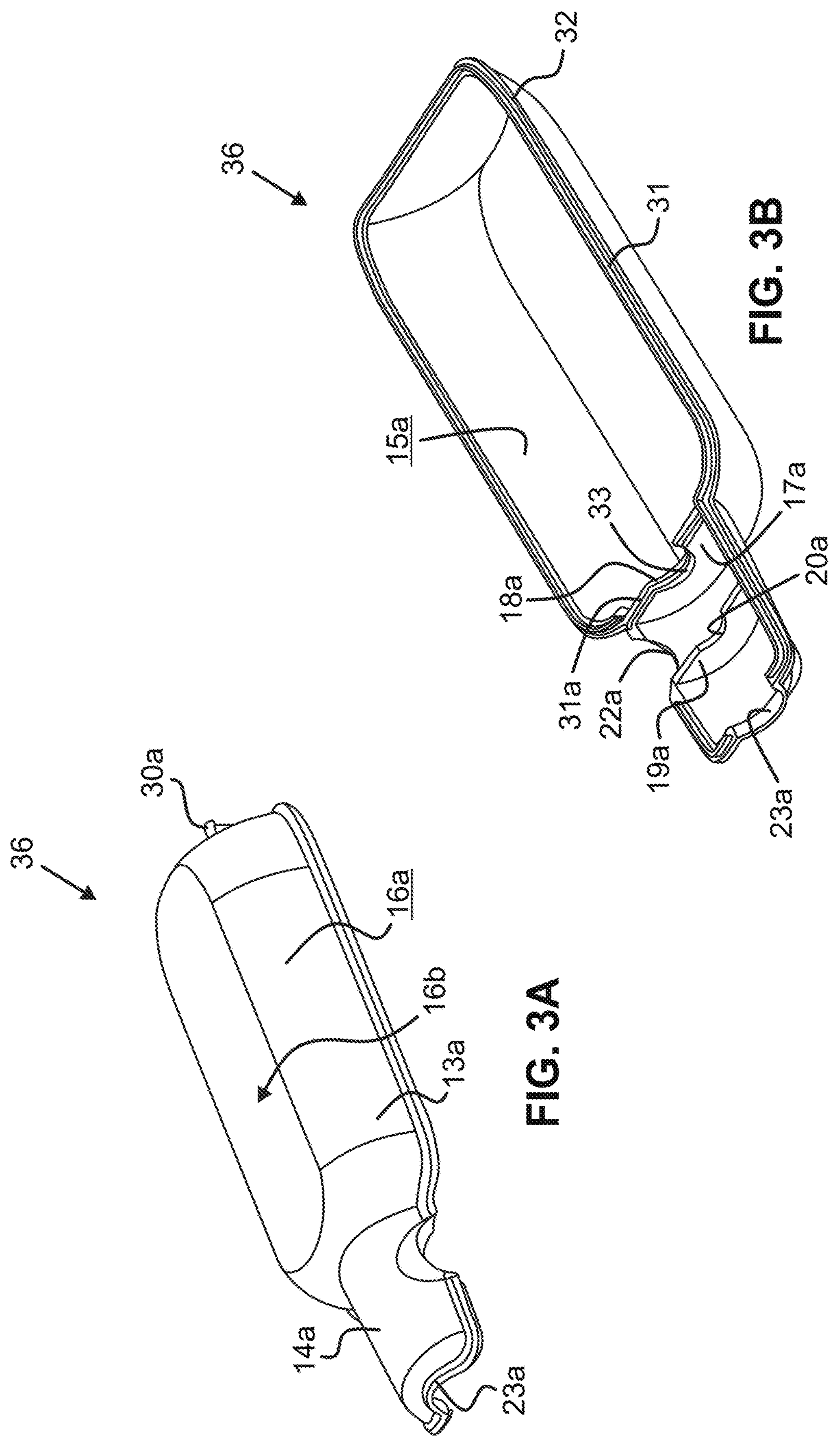
FIG. 3A depicts a perspective view of a second half-shell of the assembly in FIG. 1.
FIG. 3B depicts a perspective view of the half-shell in FIG. 3A from a different point of view.

Similarly to the first half-shell 3*a*, the second half-shell 3*b*, shown in FIGS. 3A and 3B, is formed by a first shell portion 13*a* of greater width and by a second shell portion 14*a* of smaller width and comprises an inner surface 15*a*, an outer surface 16*a* and an edge 31 connecting them. Similarly to the first half-shell 3*a*, the first shell portion 13*a* is configured to accommodate the elastomeric pump 4, 104, while the second shell portion 14*a* is configured to accommodate the assembly formed by the open end 4*b*, 104*b* of the elastomeric pump 4, 104, the second tubular portion 5*b*, 105*b* of the cannula 5, 105 with the fitting 5*c*, 105*c* and by the filling valve 6.

The edge 31 comprises a ridge 32, visible in FIG. 7, running along the perimeter of the half-shell 3*b* and shaped to couple with the groove 24 of the edge 21 of the first half-shell 3*a*.

The inner surface 15*a*, at the junction point between the first shell portion 13*a* and the second shell portion 14*a*, comprises a first rib 17*a* comprising a semicircular recess 18*a*, of such shape and size as to accommodate a semi-cylindrical portion of the assembly formed by the elastomeric pump 4, 104 and the second tubular portion 5*b*, 105*b* of the cannula 5, 105. The edge 31*a* of the first rib 17*a* comprises a ridge 32 in continuation of the ridge 32 placed on the edge 31 of the half-shell 3*b*. The edge 33 of the recess 18*a* comprises a ridge 25*a* similarly to the recess 18 of the first half-shell 3*a* (FIG. 8).

In embodiments, the inner surface 15*a* of the second shell-like portion 14*a* further comprises a second rib 19*a* comprising a respective recess 20*a* of such shape and size as to accommodate a semi-cylindrical portion of the assembly formed by the second tubular portion 5*b*, 105*b* of the cannula 5, 105 and the filling valve 6.

The second rib 19*a* can also be omitted, as shown in FIG. 1.

At the second shell-like portion 14*a*, the edge 31 comprises a first semicircular groove 22*a* to house the open end of the fitting 5*c*, 105*c* of the cannula 5, 105 and a second semicircular groove 23*a* to house the filling valve 6.

The outer surface 16*a* of the second half-shell 3*b* can comprise a flat portion 16*b* for applying adhesive labels. The outer surface 16*a* can also comprise feet 30*a* corresponding to the feet 30 of the first half-shell 3*a*, adapted to form a vertical support for the assembly 1.

Assembling the various parts to form the assembly 1 according to the invention, shown in FIG. 6, includes coupling the respective edges 31, 31 of the two half-shells 3*a*, 3*b*, as shown in FIG. 7, and then ultrasonic welding. FIG. 8 shows the detail of the coupling of the edges 25, 33 of the recesses 18, 18*a* with the outer surface of the elastomeric pump 4, 104, in a position near the open end 4*b*, 104*b* of the elastomeric pump. The ridges 25*a* of the respective edges 25, 33 operate a sealing pressure on the elastomeric material, which is completed by an ultrasonic welding.

The advantages of the infusion device assembly according to the invention clearly appear from the above description.

In fact, sealingly assembling the assembly is considerably simplified, especially in the embodiment shown in FIG. 1, since it is the housing 3 itself which ensures the sealing of the junctions between cannula 5, 105 and elastomeric pump 4, 104. Therefore, the operations of assembling, gluing and/or welding parts are saved and the assembly is compact and of low cost.

It is apparent that only some particular embodiments of the present invention have been described, to which those skilled in the art will be able to make all of the necessary changes for the adaptation thereof to particular applications, without however departing from the scope of protection of the present invention as defined in the appended claims.

The invention claimed is:

1. A medical solution infusion device assembly, comprising an infusion device and a housing containing the infusion device, the infusion device comprising an elastomeric pump having a closed end and an open end, a cannula and a filling valve configured to fill the elastomeric pump with a medical solution, wherein the housing of the infusion device comprises a first half-shell and a second half-shell, configured to be sealingly coupled to each other, the first half-shell and the second half-shell being further configured to be sealingly coupled to the infusion device in a position adjacent to the open end of the elastomeric pump;

wherein the cannula comprises a first tubular portion, a second tubular portion, and a fitting protruding perpendicularly at the second tubular portion, the first tubular portion having a smaller diameter than a diameter of the second tubular portion, so that a shoulder is placed at a junction of the first tubular portion and the second tubular portion, wherein each of the first half-shell and the second half-shell are formed by a first shell portion and a second shell portion of smaller width than a width of the first shell portion, and each of the first and second half-shells comprise an inner surface, an outer surface, and a first edge which connects the first shell portion and the second shell portion, said first shell portion being configured to accommodate the elastomeric pump, wherein said second shell portion is configured to house a set comprising the open end of the elastomeric pump, the second tubular portion of the cannula with the fitting, and the filling valve.

2. The assembly according to claim 1, wherein the first tubular portion comprises a plurality of through holes which put an interior of the cannula in communication with an interior of the elastomeric pump, allowing filling and emptying of the cannula.

3. The assembly according to claim 1, wherein the first tubular portion comprises a protruding ring.

4. The assembly according to claim 1, wherein the fitting originates from the second tubular portion of the cannula and extends perpendicular therefrom, ending with an open end, configured to be coupled to an infusion line.

5. The assembly according to claim 1, wherein the first edge of the first half-shell comprises a groove and the first edge of the second half-shell comprises a first ridge, the groove and the first ridge configured to be sealingly coupled to each other.

6. The assembly according to claim 5, wherein the inner surface of each of the first and second half-shells, at the junction point between the first shell portion and the second shell portion, comprises a first rib comprising a semicircular recess, the semicircular recess is configured to accommodate a semi-cylindrical portion of the set, a second edge of the first rib of the first half-shell comprises a groove in continuation of the groove placed on the first edge of the first half-shell, wherein a second edge of the first rib of the second half-shell comprises a second ridge in continuation of the first ridge of the first edge of the second half-shell and wherein a third edge of the recess comprises a third ridge.

7. The assembly according to claim 1, wherein the inner surface of the second shell portion or the first shell portion comprises a second rib comprising a respective recess of a shape and size to accommodate a semi-cylindrical portion of the set.

8. The assembly according to claim 1, wherein the inner surface of the first half-shell comprises a seat for a hygroscopic filter.

9. The assembly according to claim 1, wherein the first and second half-shells comprise feet for vertically supporting the assembly and/or the first half-shell comprises feet for horizontally supporting the assembly and/or the outer surface of the second half-shell comprises a flat portion for an application of adhesive labels.

10. The assembly according to claim 1, wherein the elastomeric pump is made of a thermoplastic elastomer and is free of polyvinyl chloride.

11. The assembly according to claim 1, wherein the fitting originates from the second tubular portion of the cannula and extends perpendicular therefrom, ending with an open end, flared in shape, configured to be coupled to an infusion line.

12. The assembly according to claim 1, wherein the elastomeric pump is made of a thermoplastic elastomer, and wherein the thermoplastic elastomer comprises a hydrogenated polystyrene block copolymer with polyolefins.

13. The assembly according to claim 1, wherein the outer surface of the first half-shell comprises a seat for a hygroscopic filter and a hook for suspending the assembly and/or a seat for a strap.

* * * * *